United States Patent

Warburton

[11] Patent Number: 6,096,186
[45] Date of Patent: Aug. 1, 2000

[54] METHOD FOR DETERMINING EXHAUSTION OF AN ELECTROCHEMICAL GAS SENSOR

[75] Inventor: P. Richard Warburton, Moon Township, Pa.

[73] Assignee: Industrial Scientific Corporation, Oakdale, Pa.

[21] Appl. No.: 09/135,058

[22] Filed: Aug. 18, 1998

[51] Int. Cl.[7] ................................................. G01N 27/404
[52] U.S. Cl. .......................... 205/782; 205/775; 204/401; 73/1.06
[58] Field of Search ..................................... 204/401, 431; 205/775, 782, 782.5, 783; 73/1.06; 429/90.93; 324/430

[56] References Cited

U.S. PATENT DOCUMENTS

| | | |
|---|---|---|
| 3,984,762 | 10/1976 | Dowgiallo, Jr. et al. ................ 324/430 |
| 4,029,563 | 6/1977 | Binder et al. . |
| 4,085,024 | 4/1978 | Lawson . |
| 4,116,612 | 9/1978 | Melgaard . |
| 4,127,462 | 11/1978 | Blurton et al. . |
| 4,132,616 | 1/1979 | Tantram et al. . |
| 4,151,738 | 5/1979 | Hyer et al. . |
| 4,324,632 | 4/1982 | Tantram et al. . |
| 4,384,925 | 5/1983 | Stetter et al. . |
| 4,443,763 | 4/1984 | Marsoner ................................. 204/401 |
| 4,446,000 | 5/1984 | Cullinane, Jr. . |
| 4,495,051 | 1/1985 | Fujita et al. . |
| 4,532,013 | 7/1985 | Dietz et al. ............................... 204/401 |
| 4,687,996 | 8/1987 | Okazaki et al. ......................... 324/436 |
| 4,743,855 | 5/1988 | Randlin et al. .......................... 324/430 |
| 4,810,352 | 3/1989 | Bone et al. . |
| 4,822,456 | 4/1989 | Bryan ....................................... 204/412 |
| 4,829,809 | 5/1989 | Tantram et al. . |
| 4,833,909 | 5/1989 | Matthiessen . |
| 4,948,496 | 8/1990 | Chand . |
| 5,100,530 | 3/1992 | Dorr et al. . |
| 5,202,637 | 4/1993 | Jones . |
| 5,239,492 | 8/1993 | Hartwig et al. . |
| 5,241,275 | 8/1993 | Fang ......................................... 324/430 |
| 5,369,364 | 11/1994 | Renirie et al. ........................... 324/430 |
| 5,558,752 | 9/1996 | Wang et al. . |
| 5,611,909 | 3/1997 | Studer . |
| 5,710,503 | 1/1998 | Sideris et al. ............................... 320/6 |
| 5,902,467 | 5/1999 | Wang et al. .............................. 204/415 |

OTHER PUBLICATIONS

Detection and Measurment of Hazardous Gases, Cullis et al, Science Reviews Ltd. 1981, pp 69–86. Month Unknown.
Measurment of Dissolved Oxygen, Hitchman, Laboratories RCA Ltd., John Wiley & Sons, Inc. 1978—pp 61, 81 and 82. Month Unknown.
Techniques and Mechanisms in Gas Sensing, Moseley et al, Adam Hilger/IOP Publishing Ltd. 1991, pp 161–188. Month Unknown.
Instrumental Methods in Electrochemistry, R. Greef et al, Ellis Horwood Limited 1985, pp 22–24. Month Unknown.
Amperometric Gas Sensors, Chang et al, Pergamon Press Ltd., 1993, pp 461–477. Month Unknown.
Product Data Handbook, Issue 4.0, vol. 1: Safety, Jan. 1997, City Technology Limited, p. 5.
A World of Gases . . A Single Transmitter, Unisens, Analytical Technology, Inc. Month, Year Unknown.

Primary Examiner—Robert J. Warden, Sr.
Assistant Examiner—Kaj K. Olsen
Attorney, Agent, or Firm—Dennison, Scheiner, Schultz & Wakeman

[57] ABSTRACT

A method by which an oxygen measuring instrument can test the functionality of the oxygen sensor. Oxygen sensors of the galvanic type operate by consumption of an internal easily oxidizable anode, such as lead or cadmium. Failure of the sensor due to complete consumption of all of the anode material, such that the oxygen sensor is no longer able to detect oxygen, is often rapid with little warning. This invention describes an electrical test, which may be performed in-situ on the oxygen sensor by the instrument, which provides a means for detection of an imminent failure, while the sensor is still operational.

16 Claims, 5 Drawing Sheets

METHOD FOR DETERMINING EXHAUSTION OF AN ELECTROCHEMICAL GAS SENSOR

BACKGROUND OF THE INVENTION

1. Field of the Invention

The invention relates to the field of electrochemical gas sensors having a consumable electrode, and particularly to a method for testing an operational sensor to determine if it is near to its end of useful life.

2. Description of Related Art

Over the last thirty years, instruments have become available for monitoring workplace atmospheres for hazardous gases. Atmospheres may be hazardous because of the presence of toxic gases, or combustible because of a deficiency or excess of oxygen. These gas detection instruments typically contain a gas sensor producing an electrical output signal which varies as a function of the gas concentration, and electronics to drive the sensor and to amplify and manipulate the output signal to give an auditory or visual warning or both in the event of a potentially dangerous atmosphere. Many of the present day instruments have digital displays and give a continuous output showing the gas concentrations of interest and often incorporate microprocessor controls, thus allowing more advanced features such as data logging, calculation of time weighted average exposures.

The concentration of oxygen is especially important, since if the concentration falls significantly below normal atmosphere (21% v/v at 1 atm. pressure) then insufficient oxygen will be absorbed by the blood in the lungs, resulting in decreasing oxygen concentration and impairment of judgement, nausea, vomiting, inability to move freely or cry out, and eventually convulsive movements and death (L. R. Cooper, *Oxygen Deficiency in Detection and Measurement of Hazardous Gases,* Ed. C. F. Cullis, J. G. Firth, Heinemann, London, 1981). If the oxygen concentration is too high, then the combustion of many flammable materials is facilitated, which also presents a possible hazard. Oxygen detecting instruments often have both an upper and lower concentration alarm level, typically at about 25 and 19% volume respectively.

The most common type of oxygen sensor used in instruments for monitoring workplace safety is an electrochemical sensor. The theory of operation and practical usage of electrochemical gas sensors has been discussed in detail by Chang et al. (S. C. Chang, J. R. Stetter, C. S. Cha, Talanta, *Amperometric Gas Sensors* (1993), 40, 461) and by Hobbs et al. (B. S. Hobbs, A. D. S. Tantram, R. Chan-Henry in *Techniques and Mechanisms in Gas Sensing,* Ed. P. T. Mosely, J. Norris, D. E. Williams, (1991).)

Amperometric electrochemical sensors contain at least two electrodes in contact with an electrolyte. Oxygen diffuses into the sensor through a diffusion barrier to one of the electrodes, known as the cathode. The electrons required for the reduction of the oxygen flow through the external circuit from the anode, where an equal magnitude oxidation reaction occurs. This flow of electrons constitutes an electric current, which provides the output signal. The potential of the cathode is selected such that all the oxygen which reaches the cathode is electrochemically reduced. This potential may be established by application of an external potential, thus operating the sensor in so-called polarographic mode, or by use of an anode material which is sufficiently electronegative in is the electrochemical series, such as lead or cadmium. A sensor of this latter type is known as a galvanic oxygen sensor, examples of which have been described, for example, in Lawson, U.S. Pat. No. 4,085,024, Tantram et al, U.S. Pat. Nos. 4,132,616 and 4,324,632, Culliname in U.S. Pat. No. 4,446,000, Bone et al, U.S. Pat. No. 4,810,352 and Fujita et al, U.S. Pat. No. 4,495,051.

A polarographic sensor requires an external circuit to control the potential of the sensor electrodes at a fixed value, whereas the galvanic sensor can be operated by simply placing a load resistor between the two electrodes and measuring the potential difference across this resistor, which is proportional to the current flowing through the resistor. Galvanic sensors may also be operated with a potentiostat circuit, which fixes the potential between the two electrodes. For most galvanic sensors operated in this mode, the applied potential will be zero, but other potentials may also be used.

Oxygen sensors are well known in the prior art, and polarographic and galvanic sensors have both been widely used for measuring the oxygen concentration in both gases, especially air, and in liquids (M. L. Hitchman, Measurement of Dissolved Oxygen, John Wiley & Sons, N.Y. 1978; I. Fatt, *Polarographic Oxygen Sensors, Its theory of Operation and its Application in Biology, Medicine and Technology,* Robert E. Krieger Publishing Company, Malabar, Fla. 1982).

In a typical galvanic sensor, the flow of electrons from the anode is generated by the oxidation of the anode material. For a lead anode, the reaction is believed to be oxidation of the lead to form lead oxide (PbO). The rate of oxidation depends on the amount of oxygen being reduced, which in turn depends on the rate of diffusion of oxygen into the sensor through a diffusion barrier. Since the rate of diffusion depends on the concentration of the oxygen outside the sensor, external oxygen concentration.

Since the anode is consumed in a galvanic sensor during the detection process, the sensor has a finite lifetime. Once all of the anode material has been consumed, the sensor will no longer detect oxygen. The output current of a working sensor is limited by the rate of diffusion of the oxygen into the sensor via the diffusion barrier and so the output current is independent of the state of the anode. Once the anode is consumed, then the sensor will fail and this failure often occurs rapidly, with little or no warning. When the sensor fails, the output current decreases. However, a fall in output current can be due either to a failed sensor or to the gas detection instrument being in an environment with a reduced oxygen concentration. Thus, there may be confusion about whether the sensor has failed or the oxygen concentration has decreased; this confusion is at the least very annoying and potentially dangerous.

Therefore, a method is needed to predict when a sensor will fail, before it actually does, so that a warning can be provided to the user in advance. Early warning of imminent sensor failure will allow the sensor to be replaced before it fails.

The ability to determine whether the sensor is working correctly, or to predict imminent failure is an important advantage for an instrument used for safety applications. These various problems outlined above have been addressed in the prior art to various levels of satisfaction. The most common method of ensuring that gas sensors are working correctly is frequent and periodic calibration.

Calibration is usually performed manually, by the application of calibration gases of known composition, or by exposure of the gas detection instrument to clean air. Automatic calibration methods have been described in the prior art, for example, Stetter et al in U.S. Pat. No. 4,384,925, Hyer and Roberts in U.S. Pat. No. 4,151,738, Hartwig and Habibi in U.S. Pat. No. 5,239,492 and Melgaard in U.S. Pat. No. 4,116,612 describe methods for automatic calibration of a gas detection instrument in which calibration gas are automatically applied to the sensors under the microprocessor control.

Calibration methods have also been devised in which the test gas is generated as needed, such as the electrochemical gas generators used by Analytical Technology Inc. of Oaks, Pa. 19456 (8 Page Technical Information Sheet, titled *A world of gases . . . A single, transmitter*) to provide test gas to automatically check the performance of gas detection instruments, and ensure that the sensors are responding within their specified limits. Finbow et al. in U.S. Pat. No. 5,668,302 discloses incorporating an electrochemical gas generator within an electrochemical gas sensor, behind the diffusion barrier, to provide a means for automatic function testing of the gas detection instrument.

Other methods have been devised which can achieve calibration without prior knowledge of the gas concentration, based on application of Faraday's law of electrolysis to a known volume of gas, described by Tantram and Gilbey in U.S. Pat. No. 4,829,809 and by Matthiesen in U.S. Pat. No. 4,833,909; these methods do not require a known test gas concentration.

Calibration is a very important process in gas detection, but does not provide any warning of imminent failure of a galvanic oxygen sensor. Since the failure can occur rapidly, the sensor can be successfully calibrated, only to fail a short time thereafter. Clearly a better method of determining the status of the galvanic sensor is required.

Other approaches have focused on the electrical properties of the sensor; for example Jones, U.S. Pat. No. 5,202,637 and Studer, U.S. Pat. No. 5,611,909 apply a small potential perturbation to the normally constant potential between the reference electrode and the working electrode and monitor the electrical current response of three electrode toxic gas sensors. Doer and Linowski have also described related electrical tests for HPLC electrochemical detectors in U.S. Pat. No. 5,100,530. While providing a simple, in-situ test that an instrument or controller can automatically perform on the sensor, this method will only detect those modes of sensor failure which affect the electrical properties of the working electrode, such as loss of volume due to dry-out from an aqueous based electrolyte.

Unfortunately, the failure modes of three electrode toxic gas sensors, which typically do not use consumable electrodes, are quite different from galvanic oxygen sensors, and therefore the tests described are not applicable to the latter and furthermore, the majority of these tests only indicate whether a sensor is working or not at the time of the test. What is needed is a predictive test that will provide a warning that a galvanic sensor is about to fail, but to give this warning while the sensor is still working.

A diagnostic test for exhaust gas oxygen pump sensors was described by Wang et al in U.S. Pat. No. 5,558,752. The apparatus used includes a pair of two electrode, solid, non-consumable electrolyte cells, one cell being used as an oxygen pump and the other cell providing an output signal. The test involves applying a pertubation to the potential across the pump cell, such as a low amplitude alternating current, and the resulting alternating current component of the pump cell current is used to determine if the output from the sensing cell is outside of the current limiting range of operation. This method will detect whether the sensor is no longer functioning correctly, but will not predict if the sensor will fail in the near future.

One method which has been described by Tantram et al. in U.S. Pat. No. 4,132,616 involves modifying the sensor design to include a small amount of a second metal, such as copper, within the anode, which is more electropositive than the lead, but which is still sufficiently electronegative to provide the potential to the cathode for the reduction of oxygen. Once all of the lead has been consumed, the open circuit potential of the sensor will differ between lead as the active anode material and copper as the active anode material. This method has the advantage that it is a predictive test, such that the user is warned prior to the failure of the sensor. However, this test requires modification of the galvanic oxygen sensor design, and requires sufficient time for the sensor to reach steady state open circuit potential, which may be a considerable length of time. A test which could be applied to any galvanic oxygen sensor would be much more advantageous, especially if this test could be performed periodically by a gas detection instrument with little or no need for human intervention.

Another method for predicting the failure of a galvanic oxygen cell was described by Parker in U.S. Pat. No. 5,405,512, in which the sensor is modified to include two or more anodes with a switching circuit to connect them in turn to the single cathode. While this method does provide a predictive test for failure of the galvanic oxygen sensor, it also requires the use of a novel and complex sensor design, and is not compatible with most of the sensors currently in use.

SUMMARY OF THE INVENTION

This invention describes a method that allows prediction of the imminent failure of a galvanic oxygen cell. Since galvanic oxygen cells fail suddenly and with little prior warning, this method which can be incorporated into an instrument design to allow an automated test, offers an advantage over the prior art. The method involves application of the potential difference between the two electrodes and comparing the steady state current to that of the cell in clear air without the applied potential difference potential. If these two currents are similar, within predefined limits, then the sensor is functioning correctly. If the current is outside of the predefined limit, then the test indicates that the sensor will fail soon after.

In another embodiment of this invention, the value of the load resistor is changed to a high value, and again the steady state output current flowing through the high value load resistor to that of the normal load resistor is compared. If these two currents are similar, within predefined limits, then the sensor is functioning correctly. If the current is outside of the predefined limit, then the sensor will fail soon after.

In yet another embodiment of the invention, it has been found that changes in the electrochemical impedance spectrum can be used to predict the imminent end of life of a galvanic oxygen sensor. As the sensor reaches the end of its life, the impedance at frequencies greater than 1 Hz are found to increase in value.

DESCRIPTION OF THE PREFERRED EMBODIMENTS

Figure 1:
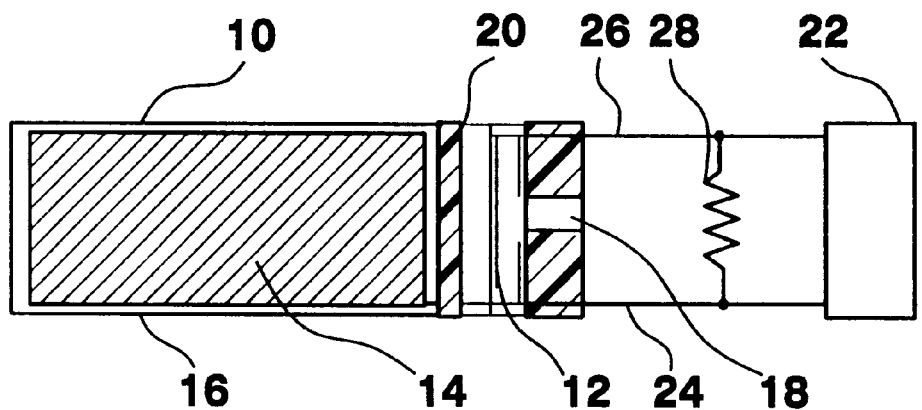
FIG. 1 is a schematic cross-sectional view of a typical galvanic oxygen sensor.

For the purposes of explanation of this invention, the principle components of a typical Galvanic oxygen sensor are shown in FIG. 1. Oxygen sensor 10 includes two electrodes 12 and 14, in contact with an aqueous electrolyte (not shown), inside a sealed container 16. The container 16 is gas tight, apart from a well defined gas diffusion barrier 18, which is commonly a capillary, a sintered material or a gas permeable membrane. One electrode, cathode 12, is located adjacent to the diffusion barrier 18, whereas the other electrode, anode 14, is located remote from cathode 12. The anode 14 and the cathode 12 are kept apart by a separator 20 and are connected to external circuitry 22 by contacts 24 and 26 respectively; these contacts 24 and 26 may be wires, solder tags or pins.

Oxygen from the outside air diffuses into the sensor 10 through the diffusion barrier 18, to the cathode 12, where it is quantitatively reduced. For the sensor 10 to function correctly, the cathode 12 is held at an electrochemical potential at which oxygen is quantitatively reduced. This potential is provided by the concurrent oxidation of the anode 14, which is fabricated from a metal which is sufficiently electronegative to be able to reduce oxygen, but which is stable in the aqueous electrolyte in the absence of oxygen. Typical materials are lead or cadmium, usually in a high surface area form such as a wool or shot.

As oxygen is reduced at the cathode 12, four electrons per oxygen molecule are consumed. These electrons are supplied by the oxidation of the anode 14, such that the rate of oxidation of the anode 14 equals the rate of reduction of the oxygen at the cathode 12. This flow of electrons from the anode 14 to the cathode 12 constitutes an electrical current i which flows through load resistor 28. The rate of oxygen reduction is limited by the amount of oxygen that reaches the cathode 12 by diffusion through the diffusion barrier 18 from the external atmosphere. Since the rate of diffusion depends on the oxygen concentration gradient between the inside of the sensor 10 (held near zero at the cathode 12) and the external atmosphere, the output current i depends on the concentration of oxygen in the external atmosphere. This current i is measured as a potential across the load resistor 28 by a conventional external circuit 22, and the resulting signal is electronically processed to give a visual indication of the oxygen concentration, activate alarms as necessary etc. depending on the design of the instrument.

The detection of oxygen therefore results in the consumption of the anode 14, and once the entirety of the anode 14 has been consumed, the sensor stops working. For a galvanic sensor 10, the open circuit potential $E_{oc}$ will be determined by the difference between the electrochemical half cell reactions of the oxidation of the anode 14 and the reduction of oxygen at the cathode 12:

$$PbO+H_2O+2e=Pb+2OH^-  E°=-0.580 \text{ vs. SHE} \quad (1)$$

$$O_2+2H_2O+4e=4OH^-  E°=0.401 \text{ vs. SHE} \quad (2)$$

(Data for standard state conditions, from *CRC Handbook of Chemistry & Physics*, 68$^{th}$ Ed., 1987–1988, R. C. Weast, M. J. Astle, W. H. Beyer (Eds.), CRC press, Boca Raton, Fla.). Therefore, for a sensor 10 using lead as the anode material 14, $E_{oc}$ will be about 0.981 V. In practice, the open circuit potential is often less than this value (between 0.7 and 0.8 V is typical), since the conditions within the cell 10 do not exactly match the standard state conditions at which the standard half cell potentials were determined.

For an electrochemical cell, such as a galvanic oxygen sensor 10, the open circuit potential $E_{oc}$ is distributed through the electrical circuit of the cell and the load resistor as described by the equation:

$$E_{oc}=\eta_a+\eta_c+i(R_L+R_{int}) \quad (3)$$

where $\eta_a$ and $\eta_c$ are the overpotentials for the anodic and cathodic reactions respectively, $R_L$ is the load resistor 28 and $R_{int}$ is the internal resistance of the cell.

The rate of the oxidation or reduction reaction is dependent upon the exponential of the overpotential as described by the Butler Volmer Equation (*Instrumental Methods of Electrochemistry*, by the Southampton Electrochemistry Group, Ellis Horwood, Ltd, Chichester, 1985). For a new galvanic oxygen sensor 10, the overpotential needed to drive the oxidation of the anode 14, is relatively small, and so the remainder of the overpotential is at the cathode 12:

$$\eta_c=E_{oc}-(\eta_a+i(R_L+R_{int}) \quad (4)$$

It is this high overpotential at the cathode 12 which ensures that the oxygen reduction reaction is both fast and quantitative. The oxygen reduction reaction at the cathode 12 is however limited by the rate at which oxygen can diffuse into the sensor 10.

As the anode 14 is consumed, the anodic overpotential $\eta_a$, increases, which is believed to be due to the reduction in active area of the anode 14, and because of formation of thick oxide/hydroxide layers on the surface of the anode 14. As the overpotential at the anode 14 increases, the overpotential at the cathode 12 decreases concomitantly for constant open circuit potential. Provided the overpotential at the cathode 12 is greater than the minimum necessary to reduce all the oxygen reaching the cathode, this change in the overpotentials of the anode 14 and the cathode 12 will not have any significant effect on the output current i.

However, as the anode 14 reaches the end of its life, the overpotential needed to drive the anodic reaction increases rapidly, resulting in a concomitant rapid decrease in the available overpotential at the cathode 12. Eventually the cathodic overpotential $\eta_c$ is insufficient to drive the oxygen reduction reaction quantitatively and the cell fails. This failure is often very rapid, and occurs with little warning to the user.

From equation (4) it may be seen that the overpotential for the reduction of oxygen $\eta_c$ at the cathode 12 depends on the open circuit potential ($E_{oc}$), the anodic overpotential $\eta_c$ and the current (determined by the rate of oxygen diffusing into the sensor 10), the internal resistance $R_{int}$ and the load resistance $R_L$. If the load resistance is increased, then the available overpotential at the cathode 12 will decrease.

Therefore, if the load resistance $R_L$ is increased to a value such that the cathodic overpotential $\eta_c$ is still greater than the overpotential necessary for the quantitative reduction of oxygen for a new sensor, then the output current i from a new sensor will still be limited by the rate of diffusion of oxygen into the sensor 10. If load resistance $R_L$ is increased to a value such that the cathodic overpotential $\eta_c$ less than the overpotential necessary for the quantitative reduction of oxygen from a sensor approaching the end of its life, then the output current i will decrease below the current value expected if the sensor output current i is limited by diffusion.

Figure 2:
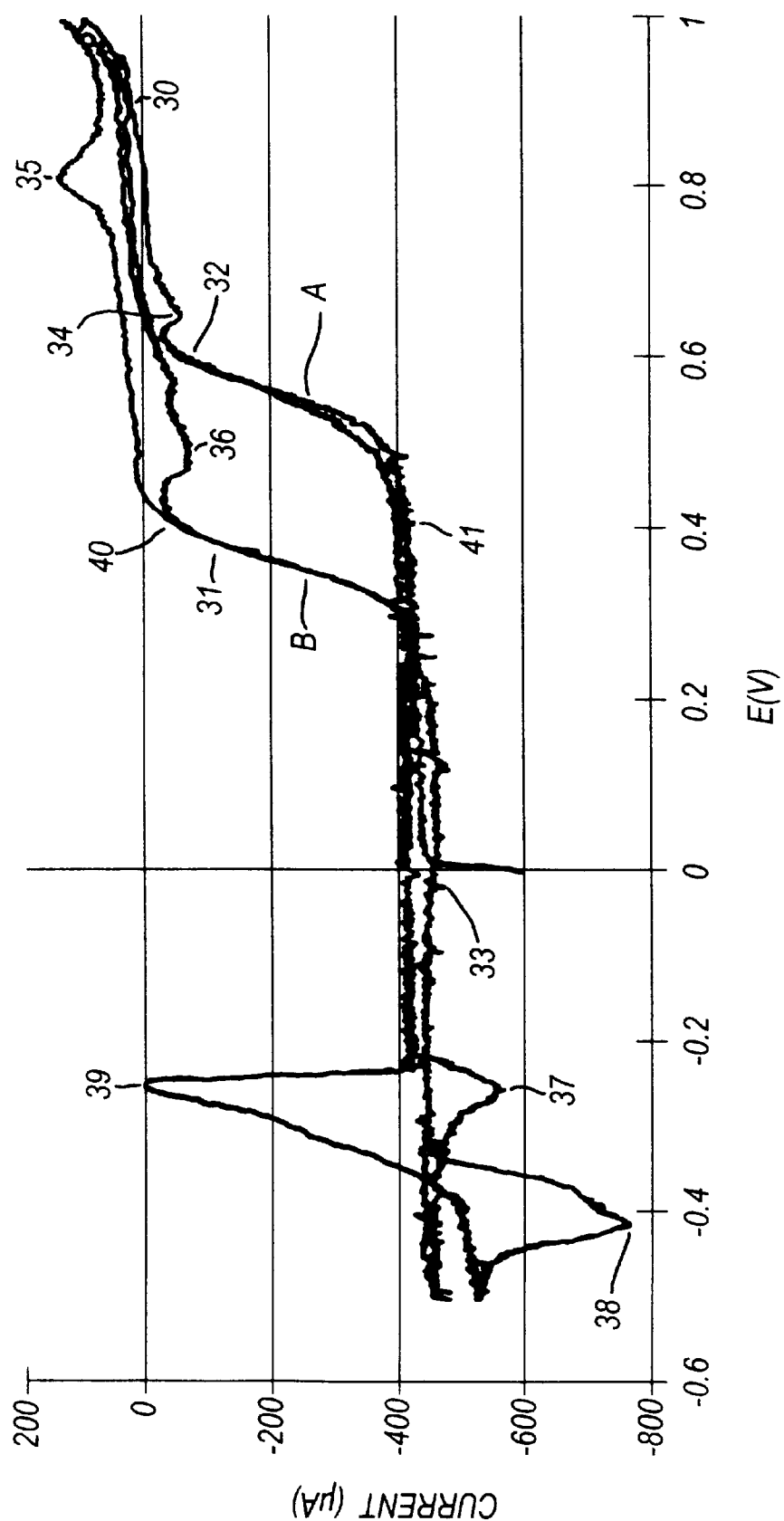
FIG. 2 is a graph of a steady state sweep (current vs. voltage) for two oxygen sensors, curve A for a new sensor, and curve B for a sensor near the end of its life.

FIG. 2 shows cyclic voltammograms for two oxygen sensors, obtained from City Technology Ltd., Portsmouth, England. The voltammograms were run at very slow scan rate, 0.05 mV/s, to approximate steady state conditions, using an EG&G (Princeton, N.Y.) PAR 273A potentiostat, interfaced with a computer running EG&G PAR 270/250 software. The voltammogram labeled A was obtained with a new sensor, whereas the voltammogram labeled B was obtained for an old sensor which was still functioning within specifications, but which was nearing the end of its operational life. The main feature of both voltammograms is the redox process corresponding to the reduction of oxygen.

At positive potentials 30, the current is close to zero, but at more negative potentials the current increases sharply (at 31 and 32) once oxygen reduction becomes possible. At still more negative potentials, for example, near zero volts, the current is on a plateau 33, and is no longer dependent upon small changes in the potential. This plateau of the oxygen reduction current 33 arises because the rate of oxygen reduction is limited by the rate of oxygen diffusion into the sensor 10. The small features at both ends of the voltammogram 34 to 39, correspond to oxidation and reduction processes of the electrodes 12 and 14 themselves and are not relevant to this discussion.

FIG. 2 clearly shows that the potential for the onset of oxygen reduction at 31 and 32 is significantly more negative for the old sensor B compared to the new sensor A. This shift in the potential for the onset of oxygen reduction at 31 and 32 is caused by the increase in the overpotential necessary for the anodic reaction $\eta_a$, as discussed above. From FIG. 2, it is apparent that at an applied potential of circa 0.4 V, there will be a current at 40 of about zero for old sensor B, whereas for the new sensor A, the current will be close to the diffusion limited current at 41. Thus even though both sensors A and B are responding to oxygen under normal operating conditions, as may be seen by the steady state current near zero volts at 33, measuring the current with an applied potential can be used to distinguish between a new sensor and a sensor which soon reach the end of its life.

In normal operation a galvanic oxygen sensor 10 is most commonly operated with a simple load resistor 28 between the electrode terminals 24 and 26. The current i which results from the reduction of oxygen within the sensor 1 flows through the load resistor 28, and the resulting voltage drop across the resistor is used to provide the output signal for the instrument.

Figure 3:
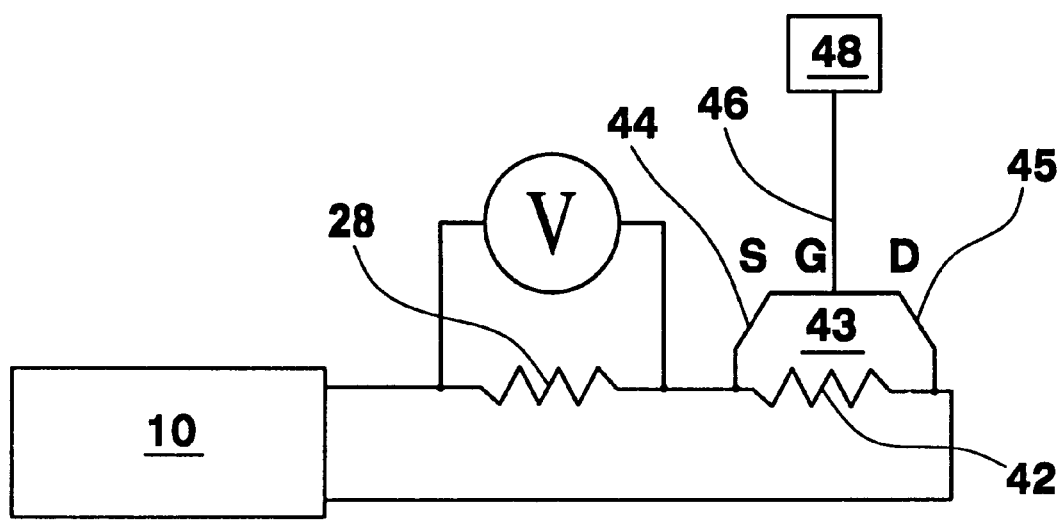
FIG. 3 is a schematic diagram of a load resistor circuit which can be used to drive a sensor for normal operation, and also to change the load resistor according to the invention.

FIG. 3 shows a circuit which will allow the resistance of the load circuit to be changed under the control of the user or a controller with the instrument, such as a microprocessor, mechanical timed controller, etc. The output from the sensor 10 is connected to the load resistor 28, across which the voltage is measured by voltmeter circuitry V which is part of the gas detection instrument. Measurement of the voltage is performed by conventional means, well known to those skilled in the art of electronics. In series with the load resistor 28 is an auxiliary resistor 42. In parallel with the auxiliary resistor 22 is a transistor 43, which is preferably a field effect transistor, having a source 44 and drain 45 connected to one side each of the auxiliary resistor 42.

The transistor 43 is selected such that when the gate 46 is held at a potential which is logically low by external circuit 48, the electrical pathway between the source 44 and the drain 45 is conductive, and provides a low impedance path around the auxiliary resistor 42. In contrast, when the gate 46 is held at a potential which is logically high by external circuit 48, the electrical pathway between the source 44 and the drain 45 is high impedance. Therefore when the potential of the gate 46 is logically low, then the auxiliary resistor 42 and the field effect transistor 43 combination add a negligible increase to the resistance of the load circuit and the resistance of the load circuit is determined by the load resistor 28.

However when the potential to the gate 46 is logically high, then the transistor 43 no longer provides a low impedance path around the auxiliary resistor 42 and the total resistance of the load on the sensor 10 is the sum of the load resistor 28 and the auxiliary resistor 42. Thus it is possible for the user, or the instrument control circuits (not shown) to change the resistance of the sensor load circuit by changing the potential of the transistor gate 46 from logical low to logical high and from logical high to logical low.

If more than one resistance change is required, it is possible to have more than one auxiliary resistor—field effect combinations (not shown) in series with the load resistor 28, each of which can be controlled by the user or the external control circuitry by controlling the logical status of the respective transistor gate potentials as described above.

The circuit shown in FIG. 3 and described above is intended for illustrative purposes only. Many other circuits are possible which will perform the same function, as is well known by those skilled in the art or electronics.

Therefore, if the steady state output currents for an operational sensor 10 are determined with the normal load resistor 28, alone, and then with a greater resistance which is the sum of normal load resistor 28 and additional resistor 42, comparison of these two output currents i and $i_{new}$ can be used to predict if the sensor 10 is approaching the end of life.

If the new output current $i_{new}$ is similar in value to the original output current i, then the sensor 10 is not near the end of its life. If the new output current $i_{new}$ is significantly less than value of the original output current i, then the sensor 10, is near the end of its life, even though the sensor 10 may still be working correctly at the time of the test. Thus this method allows the user or instrument to perform a test on the sensor 10, and predict whether that sensor is near approaching the end of its life while the sensor is still functioning. This information will allow the user to replace the sensor before it fails.

The preferred value of the additional load resistor will depend on the sensor design, and in particular on the output current i (depending on external oxygen concentration and sensor diffusion barrier 18) and the materials used to make the cathode 12 and anode 14. The cathode 12 material will determine the overpotential required for oxygen reduction $\eta_c$ and the anode 14 material will determine both the over potential for the anodic reaction $\eta_a$ and the open circuit potential $E_c$.

The optimum value of the load resistor 28 is usually recommended by the manufacturer of the sensor, for example the recommended load resistor for a C/2 oxygen sensor from City Technology Ltd. is 47 Ω (Product Data Handbook, City Technology Ltd., Jun. 1997). The optimum value of the additional load resistor 42 may be determined with reference to the example shown in FIG. 2, which uses a City Technology C/2 oxygen sensor. From curve A, it can be seen that the reduction of oxygen for the new sensor in FIG. 2 is under diffusion control for potentials negative of 0.55 V. When the potential for the reduction of oxygen under diffusion control approaches 0 V, the sensor will fail. Therefore, to predict imminent failure, a potential difference of between 0 and 0.6 V is required. To predict future failure of sensors which are working at the time of test, the preferred voltage should be greater than zero volts, if the sensor is used with a load resistor 28 alone, and for the example used above, the preferred potential is between 0.1 and 0.6 V, with the most preferred potential between 0.4 and 0.5 V.

For other types of galvanic oxygen sensors, the potential at which the oxygen reduction current becomes limited by diffusion may occur at potentials different from the sensor used in the example here.

The diffusion limited oxygen current for one of these example sensors is between 0.36 and 0.48 mA (C/2 sensor, *Product Data Handbook,* City Technology Ltd., June 1997). Assuming that the pass-fail criteria for good and bad sensors is set at a reduction in the steady state current at the preferred test potential of between 0.4 and 0.5 V to 80% of the steady state current at zero volts, the value of the additional load resistor 42 can be calculated using Ohm's Law. For the C/2 sensor described, the additional load resistor 42 should be between 1000 and 1700 Ω at the preferred test potential.

In a further embodiment of the invention, sensor 10 is operated in normal use with a large value of load resistance, for example by using the circuit shown in FIG. 3, with the gate 46 of the transistor 43 logically high, so that the resistance load on the sensor 10 is comprised of the sum of the load resistor 28 and the additional load resistor 42. For the test, the steady state current with the large value resistor is recorded and then the load resistance is decreased by changing the potential of the transistor gate 46 to logical low and recording the steady state current again. If the values of the steady state current with the large load resistance and the smaller load resistance are similar, then the sensor is working correctly. However, if the steady state current with the high value resistance is smaller than the steady state current for the lower value resistance, then the sensor is nearing the end of its life. The values of the resistors may be selected as described above. This embodiment of the invention, not only allows for periodic predictive tests to be performed on the sensor 10, but also allows the user or the instrument to discriminate between a low current output due to a low oxygen concentration and a low current output due to a failing sensor. To illustrate this aspect of the invention, if an instrument used for monitoring oxygen enters an alarm state due to low output current i from the sensor, the instrument can identify whether the low output current i is due to a failing sensor or due to a low oxygen concentration by application of this invention as described above. If the low output current i is due to the sensor approaching the end of its life, then the user can be warned of the status of the sensor, and by continuing to operate the sensor with a low load resistance, by continuing to keep the potential of the transistor gate 46 logically high, the sensor 10 can be made temporarily operational again, allowing the user a short period of time in which the sensor 10 is still functioning and may be replaced.

Changing the load resistor results in a change in the overpotential of the cathode, and there is a transient flow of current, known as charging current, which flows as a result of this change in potential. The output current is therefore the combination of the charging current and the steady state current. In order to accurately determine the change in steady state current after changing the load resistor, sufficient time should be allowed for the charging current to decay to a negligible value relative to the steady state current. For the model C/2 oxygen sensors from City Technology, the time required was less than two minutes.

If this waiting time is reduced, the charging current becomes a more significant fraction of the output current, resulting in an increased error in the steady state current determination. Since the sensor charging current behaves in a manner similar to a resistor-capacitor combination charging or discharging current, it is possible to compensate for the charging current by assuming that the charging current will decay according to a known mathematical function, such as a simple exponential decay. It is also possible to reduce the waiting time by following the decay of the charging current for a short time, then extrapolating the measured value to a longer time to obtain the steady state value. Such mathematical methods for dealing with the charging current are known to those skilled in the art; an analogous method was used by Tantram is U.S. Pat. No. 4,829,809 to calculate the total charge passed by an electrochemical sensor exposed to test gas within a small and sealed volume.

Accordingly, when the invention requires determination of a steady state value, the value can be determined by waiting for the sensor to achieve a steady state, or by taking a measurement before the sensor achieves a steady state and using this measurement to obtain an approximation of the steady state value.

Figure 4:
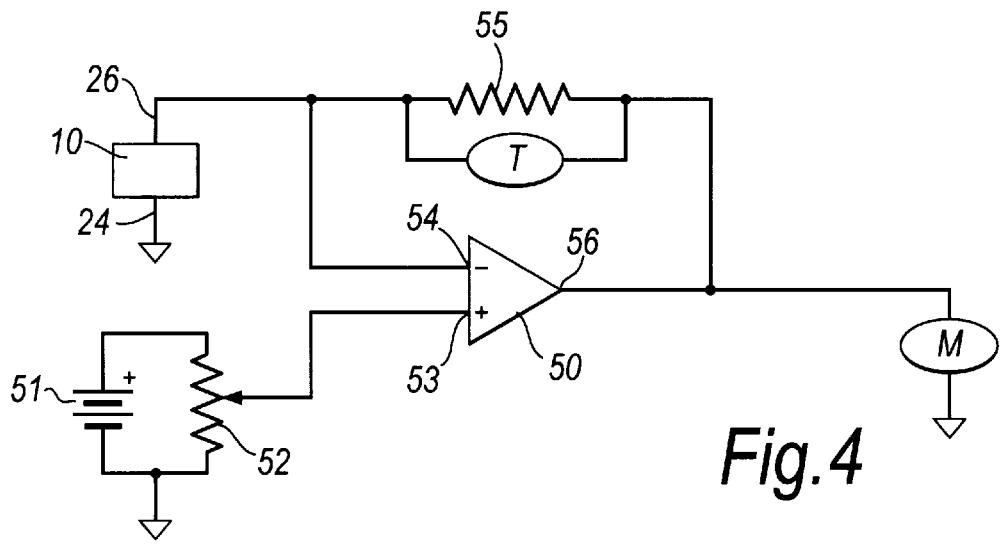
FIG. 4 is a schematic diagram of a potentiostat circuit that can be used to drive a sensor for normal operation and also to apply a potential step to a sensor according to the invention.

In another embodiment of the invention, the sensor 10 is operated in conjunction with a potentiostat circuit, such as the circuit shown in FIG. 4, in which the external circuit controls the potential across the two electrode contacts 24 and 26. The potentiostat circuit includes an operational amplifier 50 which can be any of the standard devices well known to those skilled in the electronics art, for example a Linear Technology type LT1012. The voltage at the non-inverting (plus) input 53 to operational amplifier 50 is established by fixed voltage reference 51 and variable resistor 52 to be in the desired sensor operating range of zero volts. The combination of voltage reference 51 and variable resistor 52 represents one of the many ways to produce a steady reference voltage that are known to those skilled in the art.

Sensor 10 is an oxygen sensitive device which is connected to operational amplifier 50 such that the positive terminal (cathode) 26 of sensor 10 is attached to the inverting input 54. Resistor 55 is connected between the inverting input 54 and output 56 of amplifier 50. In this configuration, the circuit functions to translate the current produced by sensor 10 into a proportionate voltage at the output 56 of amplifier 50. The voltage at output 56 of operational amplifier 50 is measured at M by conventional means well known to those skilled in the art of electronics. The potentiostat circuit shown constitutes a feedback amplifier configuration commonly known as a current-to-voltage converter.

Initially, after sensor 10 is connected to the circuit, the voltage at the inverting input 54 of amplifier 50 is forced towards the open circuit voltage of sensor 10. Since the inverting input 54 of amplifier 50 is more positive than the non-inverting input 53, the output 56 will move in a negative direction to make the voltage at the inverting input 54 equal to voltage at the non-inverting input 53, effectively discharging sensor 10 via resistor 55. The voltage at the output 56 of amplifier 50 will gradually become more positive as sensor 10 discharges, until the voltage at the inverting input 54 is equal to the voltage at the non-inverting input 53. Additionally, the current flowing through sensor 10 approaches a steady state value after the voltage at the inverting input 54 equals the voltage at the non-inverting input 53, indicating that the cell current is now controlled by the rate of oxygen diffusion into sensor 10.

A modified version of equation 3 is required to describe the behavior of the sensor 10 when it is operated in a potentiostat circuit:

$$E_{oc} + \eta_a + \eta_c + iR_{int} + E_{appl} \tag{5}$$

where $E_{appl}$ is the potential applied to the cell by the external circuit, and the other terms have the same meanings as in equation 3. For normal operation of the sensor 10, the externally applied potential $E_{appl}$ is typically zero.

Another embodiment of this invention involves applying an external potential to test whether the sensor 10 is likely to reach the end of its life soon. The optimum value of the change in potential may be calculated using the examples shown in FIG. 2. As discussed above, the reduction of oxygen for the new sensor in FIG. 2 is under diffusion control for potentials less than 0.55 V. The reduction of oxygen for the near end of life sensor in FIG. 2 is under diffusion control for potentials less than 0.30 V. When the potential for the reduction of oxygen under diffusion control approaches 0 V, the sensor will fail. Therefore to predict imminent failure, a potential difference of between 0 and 0.6 V is required, with the preferred value being between 0.1 and 0.6 V and the most preferred value being 0.4 to 0.5 V.

Therefore, if the output current i for an operational sensor is determined at the potential for normal operation (typically $E_{appl}=0$ V) and then the applied potential $E_{appl}$ is increased to test the sensor 10, the new steady state output current $i_{new}$ can be determined, and comparison of these two output signals can be used to predict if the sensor is approaching the end of life. If the new output current $i_{new}$ is similar in value to the original output current i, then the sensor 10 is not near the end of its life. If the new output current $I_{new}$ is significantly less than value of the original output current i, then the sensor 10, though still be working correctly at the time of the test, is near the end of its life.

Thus, this method allows the instrument to perform a test on the sensor 10, and predict whether that sensor is approaching the end of its life, while the sensor is still functioning. This information allows the user to replace the sensor before it fails. The preferred value of the applied potential for the test will depend on the sensor design, especially the materials used to make the cathode 12 and anode 14. The cathode 12 material will determine the minimum overpotential required for oxygen reduction and the anode 14 material will determine both the over potential for the anodic reaction $\eta_c$ and the open circuit potential $E_{oc}$. The values of the preferred potential described are for illustration and are not intended to limit the scope of this invention.

In another embodiment of this invention, more than one potential value may be used, or the potential may be changed gradually or incrementally, for example scanned over a potential range which includes the potential range 0 to 0.6 V, as illustrated in FIG. 2. Other potential waveforms may also be used, as is well known to those skilled in the art of electrochemical sensors, and the examples provided in this disclosure are not intended to limit this scope of this invention.

In another embodiment of the invention, the sensor is operated in normal use with a large value of applied potential between the sensor contacts 24 and 26, using, for example, the circuit shown in FIG. 4. For the test, the steady state current with the large value applied potential is recorded and then the applied potential is decreased and the steady state current is again recorded. If the values of the steady state current with the large applied potential and the smaller applied potential are similar, then the sensor is working correctly. However, if the steady state current with the large applied potential is smaller than the steady state current for the lower applied potential, then the sensor is nearing the end of its life. The values of the applied potentials may be selected as described below.

This embodiment of the invention, not only allows for periodic predictive tests to be performed on the sensor, but it also allows the user or the instrument to discriminate between a low current output due to a low oxygen concentration and a low current output due to a failing sensor. To illustrate this aspect of the invention, if an instrument used for monitoring oxygen enters an alarm state, due to low output current i from the sensor 10, the instrument can identify whether the low output current i is due to a failing sensor or due to a low oxygen concentration by application of this invention as described. If the low output current i is due to the sensor approaching the end of its life, then the user can be alerted to the status of the sensor 10, and by continuing to operate the sensor with a low applied potential, the sensor can be made temporarily operational, allowing the user a short period of time in which to replace the sensor.

While not essential, additional benefit may be obtained by replacing resistor 55 in FIG. 4 with a temperature sensitive network T so as to offset changes in sensor output that are due solely to temperature changes and that are not the result of changes in oxygen concentration. Such networks, consisting of temperature sensitive components such as thermistors and semiconductor devices, are well known to those skilled in the art and will be determined in practice by the temperature characteristics of the diffusion limiting mechanism in the sensor 10.

In another embodiment of this invention, since it is known that the overpotential $\eta_c$ at the cathode 12 changes with time as the anode 14 is consumed, with most of the changes in the cathodic overpotential $\eta_c$ occurring during the final stages of the anode 14 consumption, the time to failure of the sensor may be estimated based on the ratio of the current $i_{new}$ with the increased applied potential $E_{appl}$ compared to the output current i with the standard applied potential $E_{appl}$ (typically=0 V) The relationship between the ratio of output currents with the additional load resistor $i_{new}$ to the output current i for a given potential and the time interval before the sensor 10 fails will depend on the design of the oxygen cell and the material used therein and maybe found experimentally.

In another embodiment of this invention, it has been found that the conductance of the sensor 10 decreases as the cell ages, where the conductance is the inverse of the resistance. During use of the sensor 10, the anode 12 is consumed, and the resulting formation of oxide layers on the anode 12 is believed to cause the decrease of the conductance of the sensor 10 measured between the electrode contacts 24 and 26.

A conductivity meter is a device which measures the resistance or conductance between two electrodes by application of a small alternating current or alternating voltage, in contrast to most resistance meters which apply direct current or voltage signal to the object being measured. The resistance or conductance is calculated from the applied alternating current or voltage and the measured voltage or current using Ohm's law.

Resistance=voltage/current which may also be written as:

Conductance=current/voltage

The technique and apparatus for measuring the electrical conductivity of electrolytes and electrochemical cells is well known in the art, and details may be found in standard texts, such as D. A. Skoog, Principles of Instrumental Analysis, 3rd Ed., Saunders College Publishing, Philadelphia, Pa. 1985, Chapters 2 and 23, and; L. P. Hammett, *Solutions of Electrolytes with Particular Application to Quantitative Analysis,* McGraw-Hill, New York, N.Y., 1936, pp 56–62. Conductivity measurements have also been used in the prior art as a means of characterizing electrochemical gas sensors; for example carbon monoxide sensors were examined by P. R. Warburton et al in *Amperometric Gas Sensor Response Times,* Analytical Chemistry, Vol. 70 (1998), pp. 998–1006.

Figure 5:
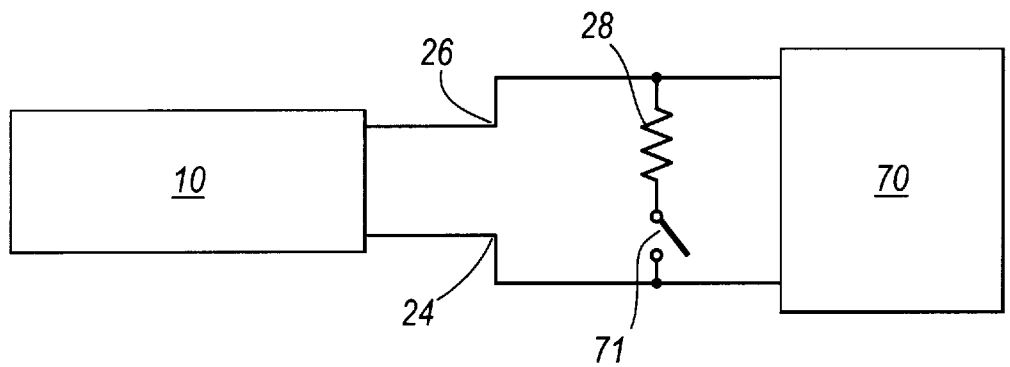
FIG. 5 is a schematic diagram of a circuit used to determine conductivity of a sensor.

The electrical conductance of the sensor 10 is readily measured using a conductivity meter, as shown, for example, as circuit 70 in FIG. 5. In the normal operation of the sensor, switch 71 remains closed, and the circuit 70 measures the potential across load resistor 28. During periodic testing of the sensor, switch 71 is opened, and the conductivity between electrodes 24 and 26 of the sensor is measured by circuit 70. On completion of the test, switch 71 is closed, and potential is again measured across the load resistor 28 as a measure of the output of the sensor.

In another embodiment of this invention it has been found that the impedance of the cell changes as the cell ages. Electrochemical impedance spectroscopy is a well established technique that has been applied to the study of many electrochemical systems. Details of the experiment and the background theory may be found in standard texts (J. R. Macdonald, *Impedance Spectroscopy, Emphasizing Solid Materials and Systems,* Publ. John Wiley & Sons, New York, (1987); A. J. Bard, L. R. Faulkner, *Electrochemical Methods, Fundamental and Applications,* Publ. John Wiley & Sons, New York, (1980), pp. 316–369).

Figure 6:
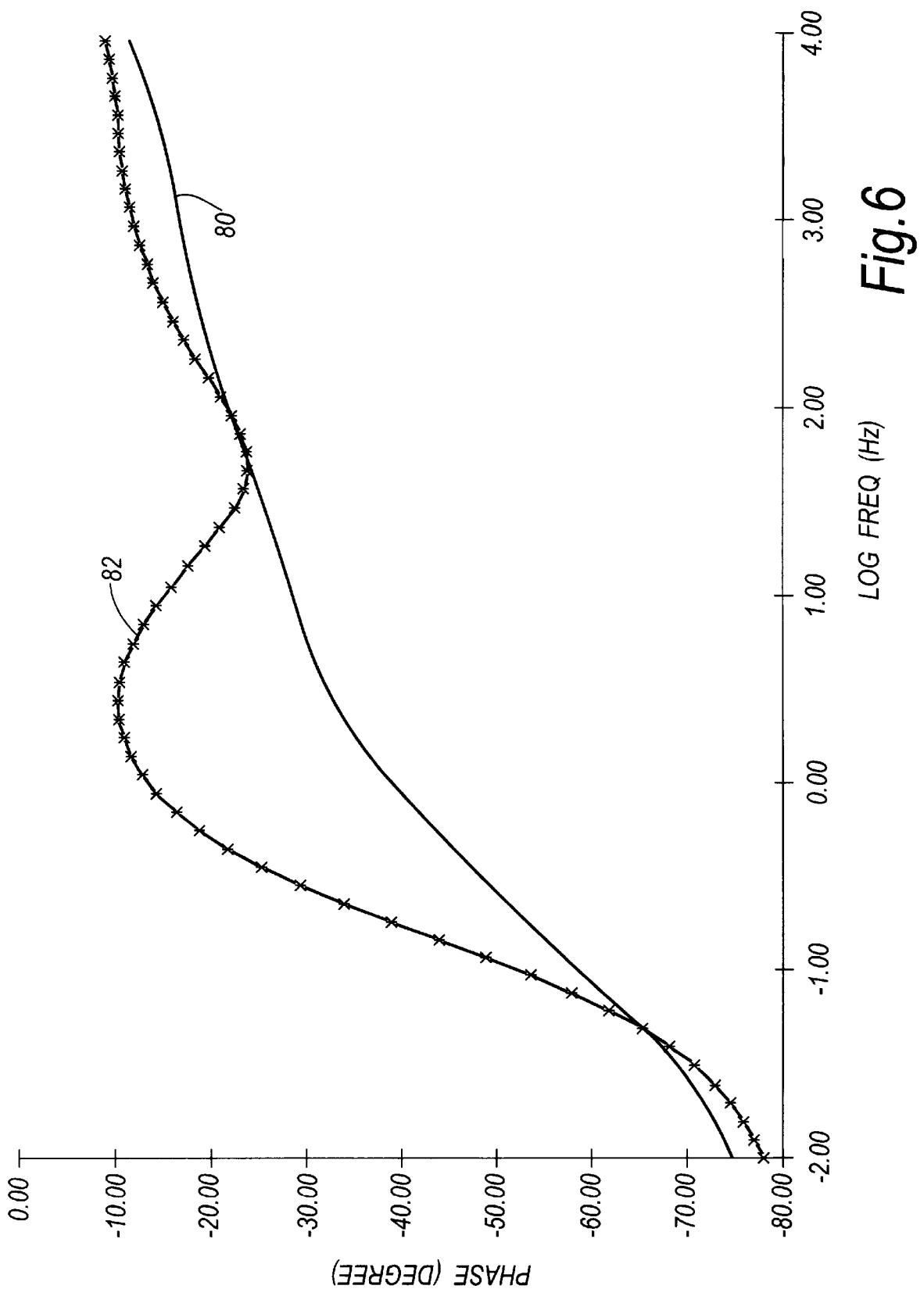
FIG. 6 is a plot of the phase angle between applied alternating voltage and resulting output current versus log frequency for a new oxygen sensor and an oxygen send of its life end of its life.
Figure 7:
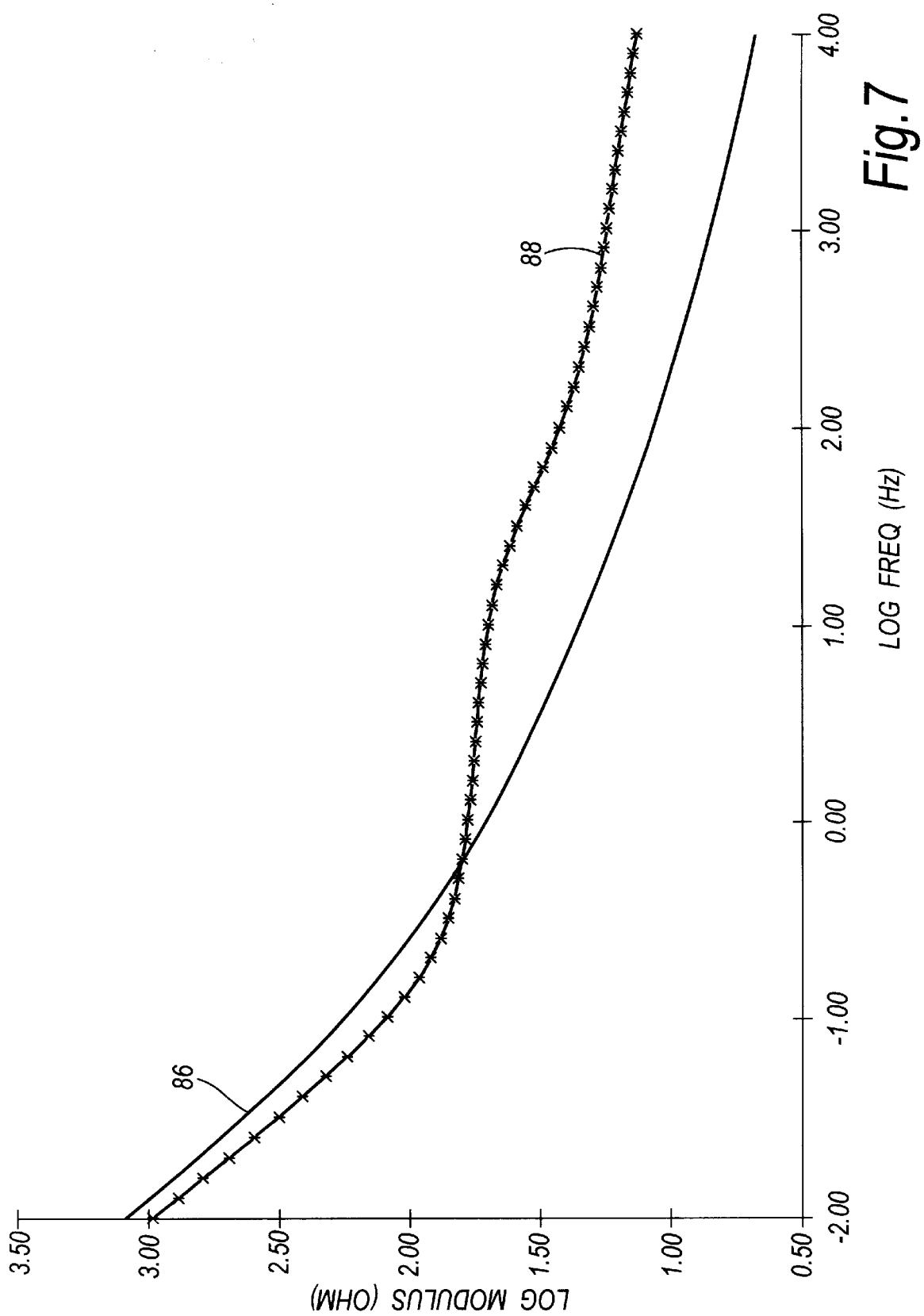
FIG. 7 is a plot of the total impedance versus log frequency for a new oxygen sensor and an oxygen sensor near the end of its life.

Electrochemical impedance spectra of new galvanic oxygen sensors and oxygen sensors nearing the end of their life were obtained using a CMS100 Electrochemical Measurement System from Gamry Instruments Inc, Warminster Pa. FIG. 6 shows the phase angle versus frequency for two galvanic oxygen sensors, one new, curve 80, and the other nearing the end of its life, curve 82. FIG. 7 shows the total impedance of these two sensors versus frequency, obtained from the same experimental runs, where the curve for the new sensor is curve 86 and the curve for the end of life sensor is curve 88.

From FIG. 6 it is evident that the phase angle increases at frequencies between 0.1 and 50 Hz, and it increases again for frequencies greater than 100 Hz. Therefore, if a small amplitude (e.g. 1 to 10 mV rms.) alternating voltage signal is applied to the sensor and the phase angle of the resulting current is measured by conventional means, this change in the phase angle can be used as a predictive test of the life of the sensor. The preferred frequency range is between 0.1 Hz and 50 Hz and frequencies greater than 100 Hz. For frequencies greater than 100,000 Hz, electromagnetic coupling to nearby metal parts can cause distortion of the electrochemical impedance measurements unless additional shielding is used. Therefore the upper limit of the preferred frequency range is 100,000 Hz, but the most preferred upper limit is below 10,000 Hz. The electrical circuits necessary to measure the phase angle of the output current in response to a small alternating voltage input to the sensor are well known in the art, and several manufacturers produce equipment capable of this measurement, such as the equipment from Gamry Instruments used to record the experimental curves shown in FIGS. 6 and 7.

The phase angle of the sensor is readily measured using a device similar to that shown in FIG. 5 where circuit 70 is substituted by appropriate circuitry, and this device may readily be incorporated as part of a complete gas detection instrument. Circuit 70 may incorporate a potentiostat circuit which controls the potential across terminals 24 and 26 during normal operation, allowing the elimination of load resistor 28 and switch 71.

From FIG. 7 it is evident that the total impedance increases at frequencies greater than about 1 Hz, and it decreases again for frequencies less than circa 0.5 Hz. Therefore, if a small ac voltage signal is applied to the sensor and the impedance of the resulting current is measured by conventional means, the impedance can be used as a predictive test of the life of the sensor. For frequencies greater than 100,000 Hz, electromagnetic coupling to nearby metal parts can cause distortion of the electrochemical impedance measurements unless additional shielding is employed. Therefore the preferred frequency range is between 1 Hz and 100,000 Hz, with a most preferred frequency range between 100 and 10,000 Hz. The electrical circuits necessary to measure the impedance of the sensor are well known in the art, and several manufacturers produce equipment capable of this measurement, such as the equipment from Gamry Instruments used to record the experimental curves shown in FIGS. 6 and 7.

The impedance of the sensor is readily measured using a device similar to that shown in FIG. 5, but with an appropriate substitution for circuit 70, and this device may readily be incorporated into a complete gas detection instrument. Circuit 70 may incorporate a potentiostat circuit which controls the potential across terminals 24 and 26 during normal operation, allowing the elimination of load resistor 28 and switch 71.

The data in FIGS. 6 and 7 show the dependence of the total impedance and the phase angle on the frequency, but this data can be presented in other formats; for example, in a so called Argand diagram, the real component of the impedance is plotted versus the imaginary component of the impedance, or both the real and the imaginary components of the impedance can be plotted as a function of frequency in a three dimensional graph. These and other representations of the data are well known in the art, (J. R. Macdonald, *Impedance Spectroscopy, Emphasizing Solid Materials and Systems,* Publ. John Wiley & Sons, New York, (1987); A. J. Bard, L. R. Faulkner, *Electrochemical Methods, Fundamental and Applications,* Publ. John Wiley & Sons, New York, (1980), pp. 316–369; *Instrumental Methods in Electrochemistry,* by the Southampton Electrochemistry Group, Publ. Ellis Horwood, Ltd, Chichester, 1985, Chapter 8) and the diagnostic tests described as part of this invention can be expressed in a variety of ways using these various known methods for expressing the data.

Figure 8:
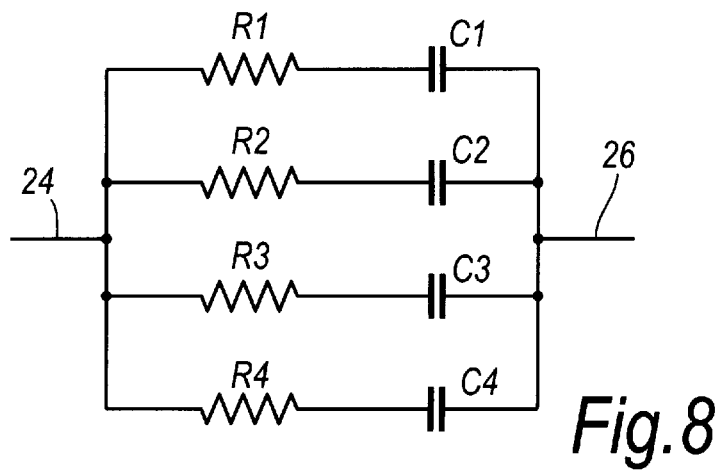
FIG. 8 is a schematic representation of an impedance model used to obtain impedance parameters for a sensor.

Alternatively, the impedance parameters of the sensor may be obtained by comparison of the total impedance and phase angle to an impedance model. An example of an typical impedance model for an electrochemical sensor is shown in FIG. 8. There are many possible impedance models available and the methods of their use are well known in the prior art (J. R. Macdonald, *Impedance*

Spectroscopy, Emphasizing Solid Materials and Systems, Publ. John Wiley & Sons, New York, (1987); A. J. Bard, L. R. Faulkner, *Electrochemical Methods, Fundamental and Applications,* Publ. John Wiley & Sons, New York, (1980), pp. 316–369; *Instrumental Methods in Electrochemistry,* by the Southampton Electrochemistry Group, Publ. Ellis Horwood, Ltd, Chichester, 1985., chapter 8). Many other impedance models can be devised, using combinations of resistors, capacitors, inductors, Warburg impedances, constant phase angle elements and other components. By fitting the model to the experimental data, numerical values can be found for the components of the model. The value of these components are found to vary with the age of the sensor and pass-fail criteria can be found experimentally.

EXAMPLE 1

A number of galvanic oxygen cells (model C/2 from City Technology) were allowed to equilibrate in air with a 50 Ω load resistor between the two electrodes. The steady state output current was measured as a potential across the load resistor with a digital multimeter, and then an additional load resistor of 1275 Ω was added in series with 50 Ω load resistor (total resistance=1325 Ω) and the output current was again recorded by measuring the potential across the 50 Ω load resistor after allowing sufficient time for the output current of the sensors to approach steady state (at least two minutes). The ratio of the output currents of each sensor with the 50Ω load resistor and with the additional load resistor ($i_{50\Omega}/i_{1325\Omega}$) was calculated.

All of the sensors tested had output currents with the 50 Ω load resistor that were within the manufacturer's specifications of this sensor, 0.42 ±0.06 mA in air, (for model C/2 sensor, City Technology Limited, Product Data Handbook, January 1997), which by Ohm's law is equivalent to a measured potential between 18 to 24 mV across the 50 Ω load resistor.

For the four new sensors, the ratio was in each case greater than 0.8. In contrast, when thirty old but still functional sensors were tested, six of them had ratios which were below the 0.8. The 6 sensors which exhibited values below 0.8 were determined to be nearing the end of their life and required replacement. The 24 sensors which exhibited high values greater than 0.8 can still be used and these sensors are not expected to fail in the imminent future.

A ratio of 0.8 was determined to be the cut-off point for usable sensors.

EXAMPLE 2

A selection of 38 galvanic oxygen cells (City Technology model C/2) were examined, 6 new cells and 32 old but functional cells. The cells were allowed to equilibrate with zero potential applied between the two electrodes using an EG&G PAR 273A potentiostat. The steady state output current for each cell was recorded; then the potential between the electrodes was then increased to 0.45 V (cathode positive with respect to the anode), and the output current was again recorded after allowing sufficient time for the output current of the sensors to approach steady state (about two minutes). The ratio of the output current for each sensor $i_{0.45V}/i_{0V}$ was calculated. All of the sensors tested had output currents at zero volts that were within the manufacturer's specifications for this sensor (0.42+/−0.06 mA in air, according to the City Technology Limited Product Data Handbook, January 1997). For the six new sensors, the average ratio $i_{0.45V}/i_{0V}$ was 89.8% with a standard error of 1.2%. In contrast, the old but still functional sensors had values which ranged from 0 to 88%, with a mean value of 58% and a standard error of 34.4%. Fifteen sensors which exhibited ratios of less than <70% were nearing the end of their life and were ready for replacement.

Seventeen sensors which exhibited ratios of between 70 and 88% were usable, and these sensors are not expected to fail in the imminent future.

EXAMPLE 3

The conductances of sensors 10 obtained from City Technology Ltd, Model C/2 were measured using a conductivity meter from YSI Inc, (Yellow Springs, Ohio), model 3100. The sensors were in three groups, new sensors as supplied by City Technology Ltd, sensors which were still working correctly but which were nearing the end of their life and sensors which has reached the end of their life and had stopped working. The conductance of the 14 sensors which had stopped working had a mean value 0f 43 mS, with a standard error of 9 mS. The 35 near end of life sensors which were still functional had a mean conductance of 91 mS, with a standard error of 15. The six new sensors all had a conductance of greater than 110 mS, which corresponds to the maximum range for this conductivity meter.

Thus, an end of life determination can be made by using a pass fail value preferably set between 50 and 90 mS, and more preferably set between 70 to 80 mS.

The set forth hereinabove is applicable to other types of galvanic sensors, and it is likely that the conductances for new, aged but still functional and failed sensors will differ from the example provided above. These criteria for other types of galvanic sensors can be established experimentally, using the procedures described.

Though this invention has been described for a galvanic oxygen sensor, it is equally applicable other galvanic sensors, whether for measuring oxygen in an gaseous atmosphere or in a liquid medium, such as water or biological fluids. This invention may also be applied to galvanic sensors for other gases, which use consumable anodes or cathodes. For galvanic sensor for gases other than oxygen, the test can be applied when the sensor is exposed to a gas which gives steady output current. For example, if a galvanic sensor for carbon monoxide or sulfur dioxide with a consumable cathode, for example, the sensors described by Binder et al in U.S. Pat. No. 4,029,563, Chand in U.S. Pat. No. 4,948,496 or by Blurton and Sedlak in U.S. Pat. No. 4,127,462, was tested using the invention described herein, the test can be performed while the sensor is exposed to an atmosphere of carbon monoxide. Such atmospheres are readily provided using gas mixtures obtained from compressed gas cylinders or other sources, and this test can be combined with a calibration of the sensors.

EXAMPLE 4

The impedance parameters of a sensor were obtained by comparison of the total impedance and to an impedance model. The impedance model used is shown in FIG. 8. This model comprises parallel combinations of resistors labeled R1, R2, R3 and R4, and capacitors labeled C1, C2, C3 and C4, in series. The model represents a sensor between the two electrodes, 26 and 24 of the sensor 10. The electrochemical impedance spectrum was obtained for new sensors (model C/2 from City Technology Ltd., Portsmouth England), working sensors nearing the end of their working lives and sensors which have failed. The experimental data and modeling to the impedance model were obtained using a CMS100 Electrochemical Measurement System from Gamry Instruments Inc., Warminster Pa. For each sensor, the model shown in FIG. 8 was fitted to the electrochemical impedance spectrum and the numerical values were obtained for the parameters C1, C2, C3, C4 R1, R2, R3 and R4. The results of this modeling are summarized in the table below.

| Parameter | NEW SENSORS sample size = 10 | | WORKING SENSORS near end of life sample size = 32 | | FAILED SENSORS sample size = 7 | |
|---|---|---|---|---|---|---|
| | Mean | Standard Error | Mean | Standard Error | Mean | Standard Error |
| R1 | 16 Ω | 8 Ω | 28 Ω | 5 Ω | 42 Ω | 9 Ω |
| R2 | 20 Ω | 6 Ω | 37 Ω | 9 Ω | 47 Ω | 10 Ω |
| R3 | 34 Ω | 7 Ω | 51 Ω | 14 Ω | 600 Ω | 460 Ω |
| R4 | 194 Ω | 58 Ω | 330 Ω | 290 Ω | 25000 Ω | 15000 Ω |
| C1 | 10 mF | 3 mF | 10 mF | 6 mF | 7.0 mF | 3.8 mF |
| C2 | 0.35 mF | 0.07 mF | 0.25 mF | 0.22 mF | 0.19 mF | 0.08 mF |
| C3 | 3.8 mF | 0.8 mF | 4.3 mF | 1.7 mF | 0.8 mF | 0.2 mF |
| C4 | 8 mF | 3 mF | 7 mF | 3 mF | 1.8 mF | 2.3 mF |

Comparison of the mean values for these parameters shows that the resistance values (R1, R2, R3 and R4) increase as the sensor ages, and increase further once the sensor has reached the end of its life. Thus, any of these resistance values or combinations thereof may be used to provide a measure of the lifetime status of the oxygen sensor.

What is claimed is:

1. A method for testing an amperometric electrochemical sensor operated in a galvanic mode and comprising at least one consumable electrode, and which measures a gas which comprises a component of a fluid, said sensor producing a steady state electrical output across a load resistor which is substantially proportional to concentration of the gas in the fluid, said method comprising the steps of:
   determining an initial steady state output;
   changing the value of the load resistor;
   observing the change in the steady state output after said changing the value of said load resistor; and
   using said change in steady state output to determine whether the sensor is near the end of its useful life.

2. The method of claim 1, wherein the steady state output is measured as current.

3. The method of claim 2, wherein the ratio of the change in output current to steady state current is determined with the change in value of the load resistor, and correlated to time before sensor failure.

4. The method of claim 1, comprising providing a plurality of load resistors in series across the output.

5. The method of claim 1, wherein the load resistor comprises a scanning or variable resistor.

6. The method of claim 1, wherein the change in value comprises reducing the value of the load resistor.

7. The method of claim 1, additionally comprising reducing the load resistance to extend sensor lifetime.

8. The method of claim 1, additionally comprising providing compensating circuitry for sensor temperature.

9. The method of claim 1, wherein the sensor is an element of a gas detection instrument.

10. A method for testing an amperometric electrochemical sensor operated with a constant potential applied to its electrodes, comprising at least one consumable electrode and which measures a gas which comprises a component of a fluid and which gives a steady state electrical output across said electrodes which is substantially proportional to the concentration of the gas in the fluid, the method comprising:
    obtaining a first steady state electrical output at a first applied potential;
    changing the value of the applied potential;
    obtaining a new steady state electrical output after said change in said applied potential; and
    computing a ratio of said new steady state electrical output to said first steady state electrical output to determine whether the said sensor is near the end of its useful life.

11. The method of claim 10, comprising changing the value in more than one step.

12. The method of claim 10, additionally comprising scanning the potential.

13. The method of claim 10, wherein said change in value comprises reducing the value of the applied potential.

14. The method of claim 10, additionally comprising reducing the value of the applied potential in order to extend sensor life.

15. The method of claim 10, additionally comprising providing temperature compensation circuitry.

16. The method of claim 10, wherein the sensor is an element of a gas detection instrument.

* * * * *